US006261823B1

(12) United States Patent
Tang et al.

(10) Patent No.: US 6,261,823 B1
(45) Date of Patent: *Jul. 17, 2001

(54) METHODS FOR PURIFYING VIRUSES

(75) Inventors: John Chu-Tay Tang, Livingston; Gary Vellekamp, Glen Ridge; Laureano L. Bondoc, Jr., Piscataway, all of NJ (US)

(73) Assignee: Schering Corporation, Kenilworth, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,227

(22) Filed: Dec. 11, 1997

Related U.S. Application Data

(60) Provisional application No. 60/033,176, filed on Dec. 13, 1996.

(51) Int. Cl.$^7$ .................................................. C12N 5/00
(52) U.S. Cl. .................... 435/239; 435/235.1; 210/660
(58) Field of Search ................................ 435/235.1, 239; 210/660

(56) References Cited

U.S. PATENT DOCUMENTS

| 4,569,794 | | 2/1986 | Smith et al. . | |
| 5,447,859 | * | 9/1995 | Prussak | 435/239 |
| 5,480,800 | * | 1/1996 | Legoux et al. | 435/325 |
| 5,607,851 | * | 3/1997 | Pellegrini et al. | 435/236 |
| 5,705,378 | * | 1/1998 | Yoshida et al. | 435/194 |
| 5,837,520 | | 11/1998 | Shabram et al. . | |

FOREIGN PATENT DOCUMENTS

| 0302692 | 2/1989 | (EP) . |
| 0 522 291 A1 | 1/1993 | (EP) . |
| 0 593 339 A1 | 4/1994 | (EP) . |
| WO 95/11984 | 5/1995 | (WO) . |
| WO 95/16772 | 6/1995 | (WO) . |
| WO 96/22378 | 7/1996 | (WO) . |
| WO 98/22588 | 5/1998 | (WO) . |

OTHER PUBLICATIONS

Huyghe, et al. Human Gene Therapy 6: 1403–1416 (1995).
Philipson, "Separation on DEAE cellulose of components associated with adenovirus reproduction," *Virology*, 19:459–465 (1960).
Philipson, "Chromatographic and Membrane Separation," chapter 6, pp. 171–233 in *Methods in Virology*, Marmorosch and Koprowski eds., Academic Press, New York and London (1967).
Albrechten et al., "Purification of plant virus coat proteins by high performance liquid chromatography," J. Virological Methods, 28:245–256 (1990).
Hewish et al., "Purification of Barley Yellow Dwarf virus by gel filtration on Shephracyl S–1000 superfine," 7:223–228 (1983).

Haruna et al., "Separation of a adenovirus by chromatography on DEAE–cellulose," *Virology* , 13:264–267 (16961).
Kanegae , et al., "A simple and efficient method for purification of infectious recombinant adenovirus," *Jpn. J. Med. Sci., Biol.*, (Abstract only) 47 (3): 157–66 (1994).
Crooks et al., "The use of size exclusion chromatography has not yet become widespread, but it currently being employed for large scale production of recombinant retrovirus," *J. Chrom.*, 502:59–68 (1990).
Mento, S.J. Viagene, Inc., as reporpted at the 1994 Williamsburg Bioprocessing Conference.
Klemperer and Pereir, *Virology*, "Study kof Adenovirus antigen fractionation by chromatography on DEAE cellulose," 9.536–545 (1959).
Belew et al., Anal. Biochem, High performance analytical applications of immobilized metal ion affinity chromatography 164:457–465 (1987).
Kato et al., J. Chron, "High–performance metal chelate affinity chromatography of proteins" 354:511–517 (1986).
Nikolaeva, et al., Abstract of S–kh Biol. (10) 75–78 (1985).
Hjorth and Moreno–Lopez J., "Purification of bovine papilloma virus by gel filtration on Sephacryl S–1000 Superfine," 5:151–158 (1982).
Gekko, K. et al., Biochemistry, 20 4677–4686 (1981).
Gekko, K. et al., *J. Biochem.*, 107, pp. 572–577 (1990).
Chang L. T. et al., "Manual of Industrial Microbiology and Biotechnology," (Demain, A.L. and N.A. Solomon, eds.) p. 466 (1986).
Fukumoto, et al., BIOSIS Abstract of Ann. Phytopathol Soc., Jpn. 49 (2) 229 (1983).
Nair, et al., Indian Vet. J., 65 (3) 183–187 (1988).
Kounounguissa, et al., J. Phytopathol Soc. Jpn. 49 (2) 220 (1983).
House et al., *Journal of Veterinary Diagnostic Investigation* on, 2 (1) 44–50 (1990).
Ferris, et al., *Journal of General Virology*, 48 (Pt. 2) 411–415 (1980).
Abdelmoeti, et al., Vaextskyddsrapporter, Avti., 3 (3) (19779).
Gupta, et al., *Vaccine*, 14 (15) 1417–20 (1996).
Franks, F., "Conformational Stability of Proteins," Chapter 11 in k*Protein Biotechnology*, (F. Franks, ed.) pp. 395–436 (Humana Press, 1993).
Gherna, R. L., "Manual of Methods for General Bacteriology," (Dermain, A.L. and N.A. Solomon, eds.) pp. 208–271 (1981).
Heckly, R. J., "Advances in Applied Microbiology," 24, pp. 1–53 (1978).
Hill, Abstract of Proc. Int. Wildl. Dis. Conf. 445–52 (1975) in Wildlife Diseases, Page (Ed.) Plenum Press, New York and London.
Nylendo, et al., Appl. Microbiol. 27 (1) 72–77 (1974).
Philipson, "Adenovirus assay by the flourescent cell–counting procedure," *Virology*, 15:263–268 (1961).

\* cited by examiner

*Primary Examiner*—Leon B. Lankford, Jr.
(74) *Attorney, Agent, or Firm*—James M. Gould; David B. Schram

(57) ABSTRACT

The invention provides methods for purifying a virus from impurities in an aqueous medium.

14 Claims, No Drawings

METHODS FOR PURIFYING VIRUSES

This application claims the benefit of Provisional Ser. No. 60/033,176 filed Dec. 13, 1996.

BACKGROUND OF THE INVENTION

The cultivation and purification of viruses has become increasingly important for gene therapy and vaccine development. Huyghe et al. (*Human Gene Therapy* 6: 1403–1416 (1995)) disclosed a comparison of several methods for purification of recombinant adenoviruses, including anion-exchange chromatography, size exclusion chromatography, immobilized zinc affinity chromatography, ultracentrifugation, concluding that the preferred process for purification of a recombinant adenovirus is nuclease treatment of a cell lysate, followed by filtration through membrane filters, followed by DEAE chromatography, followed by zinc affinity chromatography.

In view of the ever-increasing need for purified viruses, for example for use as viral vectors for gene therapy, improved methods of purification would be highly desired.

SUMMARY OF THE INVENTION

One aspect of the invention is a method for purification of a virus preparation comprising:

a) subjecting the virus preparation to anion-exchange chromatography, wherein the virus is eluted from an anion-exchange chromatographic medium; and b) subjecting the virus product of step a to size exclusion chromatography, wherein the virus is eluted from a size exclusion chromatographic medium. The virus preparation can be a cell lysate, which can be filtered before step A. The virus can be recombinant adenovirus, such as ACN53 (disclosed in WO 95/11984).

The anion exchange medium can comprise diethylaminoethyl groups on a cross-linked agarose, cellulose, polyacrylamide or polystyrene backbone, such as FRACTOGEL™-DEAE. The size-exclusion medium can comprise a cross-linked polysaccharide, and may be a composite of cross-linked agarose and dextran. An exemplary size exclusion medium is SUPERDEX-200. The anion exchange chromatographic medium can be extensively washed before application of the virus preparation.

The size-exclusion medium can be provided in a column prepared as a salt gradient decreasing in ionic strength from the top of the column towards the bottom, the top of the column having a buffer having an ionic strength substantially identical to that of the product of step a.

A further aspect of the invention is a virus purified by the method of claim 1.

DESCRIPTION OF THE PREFERRED EMBODIMENT

The present invention relates to the purification of a virus, which may for example have been produced by cultivation in a cellular host and then liberated by lysis of the cells and separation from cellular debris. The term "virus" includes wild type, mutant, and recombinant viruses, especially adenoviral vectors for expression of heterologous nucleic acid sequences.

The embodiments of the invention fall into the general strategy of adsorption chromatography of a virus preparation followed by size exclusion chromatography. Typically the anion exchange chromatography is carried out on an anion-exchange resin consisting of basic groups in side chains attached to a macromolecular backbone. The basic groups are preferably substituted amino groups, in particular diloweralkylaminoalkyl groups where each lower alkyl group has 1 to 4, preferably 2, carbon atoms, and each alkyl group has 2 to 4, preferably 2, carbon atoms. The backbone can be composed of silica or an organic matrix, for example cross-linked agarose, cellulose, polyacrylamide or polystyrene; it is particularly preferred to use an anion exchange resin consisting of dimethylaminoethyl groups (DMAE groups) or especially of diethylaminoethyl groups (DEAE groups) on a cross-linked agarose backbone; especially preferred resins of the DEAE type are those sold under the trade name DEAE-FRACTOGEL, e.g., "FRACTOGEL™EMD DEAE-650M", and "FRACTOGEL™AE". In some embodiments of the invention, the "backbone" can be a solid support such as a bead.

The anion-exchange-resin is preferably washed extensively before loading the virus preparation to remove preservatives such as sodium azide and ethanol, and other extraneous materials, by washing the column with about 5 to 10 column volumes of a basic solution such as 50 mM NaOH /1 M NaCl, followed by about 5 to 10 column volumes of a neutralizing solution such as 50 mM HCl/1 M NaCl, followed by about 5 to 30 volumes of loading and/or elution buffers. Optionally, the column is washed with a buffer of lower salt concentration than the loading and/or elution buffer before washing with loading and/or elution buffer.

Typically, a preparation of virus such as a cell lysate is loaded onto the chromatographic medium in a buffered solution of about pH 7.0–8.5, with a salt concentration of about 100–360 mM. The salt is typically NaCl. In some embodiments other buffers such as phosphate or Tris are used. Contaminants can be preferentially eluted by washing the column with a buffer at a salt concentration of about 250–380 mM. The virus can then be eluted by a solution with a salt concentration of about 360–600 mM. The salt is typically NaCl. Typically, about 5 to 50, more preferably about 30 volumes of buffer are used to elute the virus. Fractions may be collected and assayed for the presence of virus by measuring the $A_{260}$ or $A_{280}$ and pooling peak fractions; alternatively, the eluant containing the $A_{260}$ or $A_{280}$ peak may be collected in a single fraction. This single $A_{260}$ or $A_{280}$ fraction or pooled fractions in the eluant containing the virus are termed "anion-exchange pool" herein.

In the size-exclusion chromatography step, molecules are separated according to size in a bed packed with an inert porous medium, especially an inert gel medium, which is preferably a composite of cross-linked polysaccharides, e.g., cross-linked agarose and dextran in the form of spherical beads. Molecules larger than the largest pores in the swollen gel beads do not enter the gel beads and therefore move through the chromatographic bed fastest. Smaller molecules, which enter the gel beads to varying extent depending on their size and shape, are retarded in their passage through the bed. Molecules are thus generally eluted in the order of decreasing molecular size. Viruses, because of their large size, generally elute in the void volume. For example, adenoviruses have a diameter of approximately 80 nm. Media appropriate for size-exclusion chromatography of adenoviruses include but are not limited to such resins as G6000PWXL (TosoHaas); SB-806 (Alltech); SEPHACRYL S400 HR, SEPHACRYL S-500 HR, SEPHACRYL S-1000 SF, SEPHADEX G-200, SEPHAROSE CL-2B; SUPERDEX 200 prep grade, SUPEROSE 6 prep grade (Pharmacia); TSK 6000PWXL (Bodman), and ULTRAHYDROGEL 2000 (Waters).

"Size-exclusion" chromatography as used herein is intended to include gel filtration chromatography. A particularly preferred size-exclusion medium is that sold under the trade name "SUPERDEX 200"; see the Pharmacia Catalog, 1996, pages 338–339, code no. 17-1043-01 (bulk), or 17-1069-01 or 17-1071-01 (pre-packed columns). Since a group separation of virus from impurities of lower molecular weight is achieved, the loading volume of starting materials from the anion-exchange pool can be relatively large, e.g., up to 20%, more preferably 15%, of the bed volume.

Exemplary materials for the practice of the anion-exchange and size exclusion chromatographic steps of the invention are provided in Table I. Exemplary variables and controls are provided in Tables II and III.

TABLE I

Exemplary Materials Used In Anion-Exchange and Size Exclusion Chromatography

| Purification Step | Procedure | Solution Used |
| --- | --- | --- |
| DEAE-FRACTOGEL | Salt Adjustment | 4M NaCl |
| | Equilibration | 265 mM NaCl, 2 mM $MgCl_2$, 2% (w/v) sucrose, 50 mM sodium phosphate at pH 7.5 (Buffer A) |
| | | 50 mM NaOH, 1M NaCl |
| | | 100 mM HCl, 1M NaCl |
| | Wash 1 | 265 mM NaCl, 2 mM $MgCl_2$, 2% (w/v) sucrose, 50 mM sodium phosphate at pH 7.5 (Buffer A) |
| | Wash 2 | 265 mM NaCl, 2 mM $MgCl_2$, 2% (w/v) sucrose, 50 mM sodium phosphate at pH 7.5 (Buffer A) |
| | | 600 mM NaCl, 2 mM $MgCl_2$, 2% (w/v) sucrose, 50 mM sodium phosphate at pH 7.5 (Buffer B) |
| | Elution | 265 mM NaCl, 2 mM $MgCl_2$, 2% (w/v) sucrose, 50 mM sodium phosphate at pH 7.5 (Buffer A) |
| | | 600 mM NaCl, 2 mM $MgCl_2$, 2% (w/v) sucrose, 50 mM sodium phosphate at pH 7.5 (Buffer B) |
| SUPERDEX 200 | Equilibration | 130 mM NaCl, 2 mM $MgCl_2$, 2% (w/v) sucrose, 50 mM sodium phosphate at pH 7.5 (Buffer C) |
| | Elution | 130 mM NaCl, 2 mM $MgCl_2$, 2% (w/v) sucrose, 50 mM sodium phosphate at pH 7.5 (Buffer C) |

TABLE II

In-process Control and Operating Variables for the Anion-Exchange Chromatography

| Purification Procedure | Variable | Recommended Value |
| --- | --- | --- |
| All procedures | Temperature | 4–12° C. |
| Equilibration | Flow rate | <5 cm/mm. |
| 1) NaOH/NaCl | Volume | 5 column volumes |
| | pH of effluent | 12.0 |
| 2) HCl/NaCl | Volume | 6 column volumes |
| | pH of effluent | 8.0 |
| 3) Buffer A | Volume | 10 column volumes |
| | pH of effluent | equivalent to Buffer A ± 0.2 pH |
| Load | Flow rate | <5 cm/min |
| | Conductivity of the feed | 20–30 mS |
| Wash 1: Buffer A | Flow rate | <5 cm/min |
| | Volume | 4 column volumes |
| Wash 2: Buffer A/ Buffer B | Flow rate | <5 cm/min |
| | Volume | 8 column volumes |
| Elution: Buffer A/ Buffer B | Flow rate | <5 cm/min |
| | Volume | 30 column volumes |
| Fraction Selection | $A_{280}$ | >>background |

TABLE III

In-Process Control and Operating Variables for the Size-Exclusion Chromatography

| Purification Procedure | Variable | Recommended Value |
| --- | --- | --- |
| All procedures Equilibration: | Temperature | 4–12° C. |
| Buffer C | Flow rate | <1 cm/min |
| | Volume | 1 column volume |
| | pH of Effluent | equivalent to Buffer C ± 0.2 pH |
| Load | Flow Rate | <1 cm/min |
| | Volume | 0.2 column volumes |
| | Concentration | 30 $A_{280}$/mL |

TABLE III-continued

In-Process Control and Operating Variables for the Size-Exclusion Chromatography

| Purification Procedure | Variable | Recommended Value |
| --- | --- | --- |
| Elution: Buffer C: | Flow rate | <1 cm/min |
| | Volume | 1 column volume |
| Fraction Selection | $A_{280}$ | >>background |

In an embodiment of the invention, the virus is loaded from the anion-exchange pool onto a size-exclusion column. In some embodiments, the column is prepared with a salt gradient decreasing in ionic strength from the top towards the bottom of the column. After loading, the virus moves down through the salt gradient (since the virus is preferentially not adsorbed by the resin) and the gentle change in ionic strength avoids damage to the virus. After over taking the salt gradient, the virus is eluted in a low-salt (e.g. 0–200 mM NaCl) buffer. Such low salt buffers include, but are not limited to, formulations for long term storage or administration to patients.

In some embodiments, glycerol is added to the chromatographic buffers, such as elution buffer, or to the pooled fractions containing virus. Typically the glycerol is present in a final concentration of 5–20%, more typically 10%. Thus, in some embodiments, glycerol is present in all solutions throughout the process. In further embodiments, other excipients, such as about 2–16% sucrose, may be used in place of the glycerol.

In a preferred embodiment, the size exclusion chromatography column is equilibrated with buffer at low salt concentration, e.g., about 100 to 150 mM, especially about 130 mM NaCl. Just prior to loading the feed, a salt gradient is loaded, equivalent to a moderate fraction of the bed volume, e.g. 10 to 20%, preferably about 15%, from low salt concentration (about 130 mM NaCl) to the higher salt concentration of the feed (e.g., 400 to 450 mM NaCl, especially about 420 mM NaCl).

A simple test is performed to determine the quality of the DEAE-FRACTOGEL pool and consequently whether a salt gradient should be used. This test depends on the constancy of the $A_{320}/A_{260}$ ratio of the DEAE-FRACTOGEL pool diluted with an appropriate pH 7.5 buffer over a period of a few minutes (e.g., 5 minutes). An appropriate buffer consists of 50 mM sodium phosphate, pH 7.5, 2 mM $MgCl_2$, 2% sucrose, no NaCl. If the $A_{320}/A_{260}$ ratio remains substantially constant over a 5-minute period (e.g., if it increases by no more than 0.04), then that sample is suitable for either isocratic or salt-gradient size-exclusion chromatography. If the ratio of $A_{320}/A_{260}$ increases more than about 0.04 during that period, then that DEAE-FRACTOGEL pool is preferably performed on salt-gradient size-exclusion chromatography to improve the yield. Table IV provides exemplary materials and protocols for the use of salt gradient size exclusion chromatography.

Thus, for example, an exemplary recombinant adenovirus is that can be purified by the method of the invention is ACN53, which is disclosed in PCT patent application no. WO 95/11984.

In the first step, the ACN53 adenoviral vector is purified by anion exchange chromatography on a DEAE-column. For this, the virus is typically propagated in 293 kidney cells, harvested, and subjected to concentration and ultrafiltration. The concentrate is frozen and stored at about –20° C. until use. Frozen concentrate is thawed, clarified by filtration through a 0.45 μm filter, the conductivity of the preparation adjusted to about 250–360 mM NaCl, and subjected to DEAE chromatography. Solutions used in the chromatography are listed in Table 1.

In the second step, the ACN53 adenoviral vector is purified by size-exclusion chromatography on a SUPERDEX-200 column. Selected fractions containing virus are identified by $A_{260}$ or $A_{280}$ and pooled. The pooled fractions constitute the purified bulk ACN53 adenoviral vector which is then filtered sterile through a 0.2 μm filter and stored at about –20° C.

The virus in the DEAE-FRACTOGEL pool may be unstable due to the presence of a high concentration of salt (about 420 mM NaCl). It is preferably processed immediately or stored at 4–12° C. for not more than about 24 hours.

Fractions of the elution profile showing the ACN53 adenoviral vector peak as determined by $A_{260}$ or $A_{280}$ are pooled for further processing. The size-exclusion pool is filtered through a 0.2 μm filter. This filtrate, the final purified

TABLE IV

Exemplary materials and protocols for the use of salt gradient size exclusion chromatography.

| Step | Procedure | Typical Range | Preferred values |
|---|---|---|---|
| Step (I) | Equilibrate the column with the low salt buffer | 100 to 150 mM NaCl | 130 mM NaCl |
| Step (ii) | Generate salt gradient at top of column | (100–150) to (400–500) mM NaCl; 10 to 20% bed volume | 130 to 450 mM NaCl; 15% bed volume |
| Step (iii) | Load the DEAE-pool onto the column. | 10 to 20% bed volume | 15% bed volume |
| Step (iv) | Elute the adenovirus with high-salt solution | 400 to 500 mM NaCl | 450 mM NaCl |
| Step (v) | Complete the elution of the Virus. | 400 to 500 mM NaCl | 450 mM NaCl |

The purification method of the present invention is suitable for scaling-up (or scaling down) and for large-scale containment. Suitable procedures and guidelines well-known in the art can be used and followed to control the virus and prevent biohazardous situations: see, e.g., "Biosafety in Microbiological and Biomedical Laboratories", 3rd Edition, edited by Richman and McKinney, U.S. Department of Health and Human Services, published by the Center for Disease Control and the National Institute of Health, Washington, DC, U.S. Government Printing Office, May 1993.

The methods of the instant invention are amenable to a wide range of viruses, including but not limited to adenoviruses, pox viruses, iridoviruses, herpes viruses, papovaviruses, paramyxoviruses, orthomyxoviruses, retroviruses, and rotaviruses. The viruses are preferably recombinant viruses, but can include clinical isolates, attenuated vaccine strains, and so on.

bulk ACN53 adenoviral vector, is then transferred into sterile plastic bottles (e.g. Teflon) and stored at about –20° C. The in-process controls for this step are listed in Table III.

The increase in purity of the ACN53 adenoviral vector at each step of the purification method can be followed by Resource Q HPLC (see Huyghe et al., *Human Gene Therapy*, Vol. 6 (November 1995), pp. 1403–1416 at p. 1405). The quality of the virus in the first and second chromatographic pools is also monitored by spectroscopic methods. The characteristic ratio of $A_{260}/A_{280}$ is 1.23–1.31:1 for final purified virus. The light scattering which results from the high molecular weight of the virus is derived from the ratio of $A_{320}/A_{260}$ nm and is also used to monitor the chromatographic pools. Purified, free virus particles display a light scattering ratio of about 0.22–0.30:1.

The following Examples serve to illustrate the present invention. The selected vectors and hosts and other materials, the concentration of reagents, the temperatures, and the values of other variables are only to exemplify how the present invention may be carried out, and are not to be considered limitations thereof.

EXPERIMENTAL EXAMPLES

A. Small Scale Purification of Adenovirus (1) Anion-Exchange Chromatography (DEAE-Fractogel)

A DEAE-EMD FRACTOGEL 650M column (E. Merck), 5×18 cm., was pre eiibrated with 5 bed volumes (B.V.) of 0.5 M NaOH / 1M NaCl followed by 6 B.V. of 0.1 M HCl/1 M NaCl, and then by 20 B.V. of Buffer A (265 mM NaCl, 2 mM $MgCl_2$, 2% (w/v) sucrose, 50 mM sodium phosphate at pH 7.5) at a linear flow rate of 2 cm/min. The feed for this column was derived from 2 liters of frozen crude virus solution, which was thawed, microfiltered through a 0.45 $\mu$ membrane, and adjusted with a small volume of 4 M NaCl to a conductivity equal to that of Buffer A. The feed was loaded onto the column at a linear flow rate of 1 cm/min. The column was washed with 4 B.V. of Buffer A. The column was then washed with 8 B.V. of 94% Buffer A/6% Buffer B (identical to Buffer A except that NaCl was 600 mM). The column was eluted with 30 B.V. of a linear gradient from 94% Buffer A / 6% Buffer B to 100% Buffer B. Fractions containing substantial virus were pooled to form the feed ("DEAE pool") for the following column.

(2) Isocratic Size-Exclusion Chromatography (Superdex-200)

Size exclusion chromatography was performed on a SUPERDEX-200 column (Pharmacia), 5×73 cm, pre-equilibrated with 0.5 B.V. 0.5 M NaOH, 1 B.V. of $H_2O$, and 2 B.V. of Buffer C (130 mM NaCl, 2 mM $MgCl_2$, 2% (w/v) sucrose, 50 mM sodium phosphate at pH 7.5) at a linear flow rate of 0.6 cm/min. The feed consisting of 220 ml of DEAE pool was loaded onto the column. ACN53 was eluted with Buffer C at a linear flow rate of 0.6 cm/min. Fractions with substantial virus were pooled, passed through a 0.2 $\mu$ microfilter and stored. The virus concentrate can be stored at low temperature, e.g., at 0–10° C., preferably at about 4° C., or if the volume is small, e.g., less than about 50 ml, frozen at −80° C.

(3) Salt-Gradient Size-Exclusion Chromatography (a). Salt Dilution Test

The DEAE-FRACTOGEL pool (0.4 ml) was mixed with of a buffer consisting of 50 mM sodium phosphate, pH 7.5, 2 mM $MgCl_2$, 2% sucrose, no NaCl (0.8 ml) and immediately placed in a quartz cuvette and measured for absorbance at 260 and 320 nm on a UV spectrometer equipped with a photodiode array. Without removal of the sample from the cuvette, the reading was repeated at 1–2 minute intervals over a 5-minute period. If the ratio of $A_{320}/A_{260}$ was substantially constant during that period, then that DEAE-FRACTOGEL pool was suitable for either isocratic or salt-gradient size-exclusion chromatography. If the ratio of $A_{320}/A_{260}$ increased more than about 4% during that period, then that DEAE-FRACTOGEL pool required salt-gradient size-exclusion chromatography to improve the yield.

(b) Salt-Gradient Size-Exclusion Chromatography

A salt-gradient chromatography was performed on a SUPERDEX-200 column, 2.6 cm ×60 cm, pre-equilibrated with 0.5 B.V. 0.5 M NaOH, 1 B.V. of $H_2O$, and 2 B.V. of Buffer C (20 mM sodium phosphate, pH 8.0, 130 mM NaCl, 2mM $MgCl_2$, 2% sucrose). Immediately prior to loading the DEAE pool, a linear gradient from 100% Buffer C to 100% Buffer D (20 mM sodium phosphate, pH 8.0, 420 mM NaCl, 2 mM $MgCl_2$, 2% sucrose) of 0.15 B.V. (48 ml) was applied to the SUPERDEX-200 column. The feed consisting of 20 ml of a DEAE pool that had failed the above test was then loaded onto the column and eluted with Buffer D at a linear flow rate of 0.6 cm/min. Fractions with substantial virus eluting in or near the void volume were pooled, passed through a sterilizing filter and stored at −80° C. The step yield was 60% and the $A_{320}/A_{260}$ ratio was 0.24:1.

B. Large-Scale Purification of Adenovirus (1) Anion Exchange Chromatography

The frozen vial concentrate from the fermentation and recovery step was thawed and filtered through a 0.45 $\mu$m hydrophilic DUPAPORE membrane in a MILLIPORE 10" Opticap capsule. The filtrate was collected in a closed tank. To minimize losses, the filter cartridge was washed with about 1.5 L of buffer J-1 (50 mM sodium phosphate pH 7.5, 265 mM sodium chloride, 2 mM magnesium chloride, 2% (w/v) sucrose) supplemented with 5.4% (w/w) of solution J-3 (4 M sodium chloride). The salt concentration of the filtrate was adjusted by adding 5.4% (w/v) of solution J-3. (4 M sodium chloride). This feed solution was then applied to a FRACTOGEL EMD DEAE-650 M column (7 cm diameter, 14.8 cm bed height, 570 ml bed volume) pre-equilibrated with buffer J-1 (50 mM sodium phosphate pH 7.5, 265 mM sodium chloride, 2 mM magnesium chloride, 2% (w/v) sucrose). The Adenovirus binds to the anion exchange resin, whereas the majority of media and host cell impurities pass through the column in the spent charge. The column was initially washed with 4 bed volumes of buffer J-1 followed by a second isocratic wash of 8 bed volumes of 94% buffer J-1 and 6% buffer J-2 (50 mM sodium phosphate pH 7.5, 600 mM sodium chloride, 2 mM magnesium chloride, 2% (w/v) sucrose) to remove additional impurities. The virus was eluted from the column with a 30 bed volume linear gradient from 6% to 100% buffer J-2. The adenovirus peak of the elution profile as determined by $A_{280}$ was collected and pooled for further processing. The in-process controls and operating parameters for the anion exchange chromatography step are summarized in Table V.

TABLE V

In-Process Control and Operating Parameters for the Anion-Exchange Chromatography
Column size: 7 cm diameter, 14.8 cm bed height, 570 ml bed volume

| Purification Procedure | Parameter | Value |
| --- | --- | --- |
| All Procedures | Temperature | 3 to 9° C. |
| Equilibration | Flow Rate | 4 cm/min |
|  | Volume | 22 Column Volumes |
|  | pH of Effluent | Equal to Buffer J-1(7.4) |
| Load | Flow Rate | 1 cm/min |
|  | Conductivity of the Feed | 28.2 mS |
| Wash 1 | Flow Rate | 2 cm/min |
|  | Volume | 4 Column Volumes |
| Wash 2 | Flow Rate | 2 cm/min |
|  | Volume | 8 Column Volumes |
| Elution | Flow Rate | 2 cm/min |
|  | Volume | 30 Column Volumes |
| Fraction Selection | $A_{280}$ | Peak area |

(2) Size Exclusion Chromatography

The DEAE-Pool was applied immediately to a SUPERDEX-200 size exclusion column (14 cm diameter, 77 cm bed height, 11.9 L bed volume) pre-equilibrated with buffer K-1 (20 mM sodium phosphate pH 8.0, 100 mM sodium chloride, 2 mM magnesium chloride, 2% (w/v) sucrose). The column was eluted with buffer K-1. The adenovirus peak of the elution profile as determined by $A_{280}$ was collected and pooled. This chromatography step achieved a buffer exchange and separation of low molecular weight impurities from the adenovirus product. The in-process controls and operating parameters for the size exclusion chromatography step are summarized in Table VI.

TABLE VI

In-Process Control and Operating Parameters for the Size Exclusion Chromatography
Column size: 14 cm diameter, 77 cm bed height, 11.9L bed volume

| Purification Procedure | Parameter | Value |
| --- | --- | --- |
| All Procedures | Temperature | 3 to 9° C. |
| Equilibration | Flow Rate | 0.43 cm/min |
|  | Volume | 2.3 Column Volume |
| Load | Flow Rate | 0.43 cm/min |
|  | Volume | $\leq$0.09 Column Volumes |
|  | Concentration | 2.7 $A_{280}$/mL |
| Elution | Flow Rate | 0.43 cm/min |
|  | Volume | 1.5 Column Volume |
| Fraction Selection | $A_{280}$ | Peak area |

(3) Final 0.2 μm Filtration

The SUPERDEX 200-pool was filtered through a 0.2 μm hydrophilic DURAPORE membrane (STERICUP, MILLIPORE) at 2 to 15° C. This step was carried out under sterile conditions in a biosafety cabinet. Because several filtration devices were used, the individual filtrates were pooled and then aliquoted into autoclaved containers. The containers of bulk drug substance in solution were frozen in a dry ice/ethanol bath and stored at about −20° C.

All publications and patent applications cited herein are incorporated by reference to the same extent as if each individual publication or patent application was specifically and individually indicated to be incorporated by reference.

Modifications and variations of this invention will be apparent to those skilled in the art. The specific embodiments described herein are offered by way of example only, and the invention is not to be construed as limited thereby.

What is claimed is:

1. A method of purifying adenovirus from a virus preparation, comprising the successive steps of:
   a) subjecting the virus preparation to anion-exchange chromatography, wherein the adenovirus is eluted from an anion-exchange chromatographic medium; and
   b) subjecting the eluate of step a) which contains the adenovirus to size exclusion chromatography, wherein the adenovirus is eluted from a size exclusion chromatographic medium.

2. The method of claim 1, wherein the virus preparation is a cell lysate.

3. The method of claim 2, wherein the cell lysate is filtered before step a).

4. The method of claim 1, wherein the adenovirus is recombinant.

5. The method of claim 1 wherein the adenovirus is ACN53.

6. The method of claim 1, wherein the anion-exchange medium is DEAE-FRACTOGEL.

7. The method of claim 1, wherein the size exclusion medium is SUPERDEX-200.

8. The method of claim 1 wherein the anion-exchange medium comprises diethylaminoethyl groups on a cross-linked agarose, cellulose, polyacrylamide or polystyrene backbone.

9. The method of claim 1, wherein the size-exclusion medium comprises a cross-linked polysaccharide.

10. The method of claim 9, wherein the cross-linked polysaccharide is a composite of cross-linked agarose and dextran.

11. The method of claim 1, wherein the anion-exchange chromatographic medium is extensively washed before step a).

12. The method of claim 1, wherein step b) further comprises eluting the adenovirus from the size-exclusion chromatographic medium into a low-salt buffer by a high-salt elution buffer, wherein the size-exclusion medium is in a column containing a salt gradient which decreases in ionic strength from the top of the column towards the bottom of the column.

13. The method of claim 1, wherein the anion-exchange chromatographic medium or the size exclusion chromatographic medium is contacted with a buffer comprising glycerol, including wash, equilibration, loading and elution buffer.

14. The method of claim 1, further comprising a step of adding glycerol to a fraction which contains the adenovirus.

* * * * *